United States Patent [19]
Furuya et al.

[11] Patent Number: 5,453,374
[45] Date of Patent: Sep. 26, 1995

[54] TRIGONOPSIS TRANSFORMANT PRODUCING D-AMINO ACID OXIDASE

[75] Inventors: Kaoru Furuya, Nobeoka; Akio Matsuda, Fuji, both of Japan

[73] Assignee: Asahi Kasai Kogyo Kabushiki Kaisha, Osaka, Japan

[21] Appl. No.: 96,741

[22] Filed: Jul. 23, 1993

[30] Foreign Application Priority Data

Jul. 27, 1992 [JP] Japan .................... 4-199948

[51] Int. Cl.[6] .................... C12N 1/15; C12N 15/53; C12N 9/02; C12P 35/06
[52] U.S. Cl. .................... 435/254.11; 435/49; 435/189; 435/911; 536/23.2
[58] Field of Search ................ 435/47, 49, 189, 435/254.11, 911; 536/23.2; 935/52

[56] References Cited

U.S. PATENT DOCUMENTS 3,801,458  4/1974  Fildes et al. .................... 435/47
5,284,754  2/1994  Bayer et al. .................... 435/49

FOREIGN PATENT DOCUMENTS 0364275   4/1990   European Pat. Off. .
0409521   1/1991   European Pat. Off. .
0436355   7/1991   European Pat. Off. .
55-35118  9/1980   Japan .
62-262994 11/1987  Japan .
63-71180  3/1988   Japan .
2-200181  8/1990   Japan .
90-12110 10/1990   WIPO .

OTHER PUBLICATIONS

Verdoes et al "Glucoamylase overexpression in *Aspergillus niger* . . . " Transgenic Res. 2:84–92.
Biotechnology Leters, vol. 14, No. 3 (Mar. 1992) pp. 195–200, Huber et al.
Bio/technology, vol. 9 (Feb. 1991) pp. 188–191, Isugai et al.
Isogai et al "Structure and Expression of cDNA for D–Amino Acid Oxidase . . . " *J. Biochem.* 108:1063–1069. (1990).

Primary Examiner—Stephen G. Walsh
Attorney, Agent, or Firm—Pennie & Edmonds

[57] ABSTRACT

A *Trigonopsis variabilis* transformed with a recombinant DNA containing a D-amino acid oxidase gene capable of expressing in *Trigonopsis variabilis* is provided. A process for transforming *Trigonopsis variabilis* and a process for preparing 7-β-(5-carboxy-5-oxopenetaneamide)cephalosporanic acid by using a transformant of *Trigonopsis variabilis* are also provided. The transformant of *Trigonopsis variabilis* shows high DAO activity and low activity of an esterase which interferes with the preparation of cephalosporin C. Accordingly, the *Trigonopsis variabilis* of the present invention enables one to produce cephalosporin C.

Moreover, the *Trigonopsis variabilis* of the present invention can be used for the preparation or cephalosporin C merely by treating the cells with toluene so that large scale use is practical.

8 Claims, 10 Drawing Sheets

FIG. 1
Prior Art

Ala-Lys-Ile-Val-Val-Ile-Gly-Ala-Gly-Val-

Ala-Gly-Leu-Thr-Thr-Ala-Leu-Gln-Leu-Leu

Arg-Lys-Gly-His-Glu-Val-Thr-Ile-Val-Ser-

Glu-Phe-Thr-Pro-Gly-Asp-Leu-Ser-Ile-Gly-Tyr-

FIG. 2
Prior Art

| amino acid sequence | -Arg-Lys-Gly-His-Glu-Val- | -Glu-Phe-Thr-Pro-Gly- |
|---|---|---|
| nucleotide sequence | GT AAA GGT CAT GAA GT<br>    C  G  C    C  G<br>        A<br>        G<br>(DAO-1)<br><br>GT AAA GGA CAT GAA GT<br>    C  G  G  C  G<br>        A<br>        G<br>(DAO-2) | GAA TTT ACT CCT GG<br>     G  C  C  C<br>            A<br>            G<br>(DAO-3)<br><br>GAA TTT ACA CCT GG<br>     G  C  G  C<br>            A<br>            G<br>(DAO-4) |

FIG. 3

```
GAATTCAGAC ATGGCAGAAT TTAACGGCCA CTACAGTTGG CCGTTCGTAA ACGAGACAAG    60

TGACTCANGG CAGCACCGTC TCAGTCCACC GGTCTAAAGC ATTGGTGCCA GATGAATTTG   120

GAAACTGTCA CCTTATAGAA TTACTTTTGG ATAGTTTTTG TAAGGCTGGA GACTTGTAAG   180

CCTGACTCAT TGACTCATCG GCGAAAGCTT CCTATCTTGG AGCTAAGATC GCCTGATCGT   240

TTTGCCCTAC TTATCTTGGT TGCATGAGTT GGCCGGTCAG AGCCGCATTC TAGCCAAAGG   300

GTTATAGCGT TACACTCTTG ATAGGCAAAT CCGTGCTCGG ATTATATATA AGGCAAAAGT   360

CGATTCAACG GATCAATAAA  ATG GCT AAA ATC GTT GTT ATT GGG TAAGTGCCTG   414
                      Met Ala Lys Ile Val Val Ile Gly
                                       5
ATACCAGACG GCTGACATTG TTTAGT GCC GGT GTT GCC GGT TTA ACT ACA GCT    467
                             Ala Gly Val Ala Gly Leu Thr Thr Ala
                                      10                  15
CTT CAA CTT CTT CGT AAA GGT CAT GAG GTT ACA ATT GTG TCC GAG TTT     515
Leu Gln Leu Leu Arg Lys Gly His Glu Val Thr Ile Val Ser Glu Phe
         20                  25                  30
ACG CCC GGT GAT CTT AGT ATC GGA TAT ACC TCG CCT TGG GCA GGT GCC     563
Thr Pro Gly Asp Leu Ser Ile Gly Tyr Thr Ser Pro Trp Ala Gly Ala
     35                  40                  45
AAC TGG CTC ACA TTT TAC GAT GGA GGC AAG TTA GCC GAC TAC GAT GCC     611
Asn Trp Leu Thr Phe Thr Asp Gly Gly Lys Leu Ala Asp Tyr Asp Ala
 50                  55                  60                  65
GTC TCT TAT CCT ATC TTG CGA GAG CTG GCT CGA AGC AGC CCC GAG GCT     659
Val Ser Tyr Pro Ile Leu Arg Glu Leu Ala Arg Ser Ser Pro Glu Ala
             70                  75                  80
GGA ATT C                                                           666
Gly Ile
 83
```

FIG.5(a)
Prior Art

```
ATG GCT AAA ATC GTT GTT ATT GGT GCC GGT GTT GCC GGT TTA ACT ACA     48
Met Ala Lys Ile Val Val Ile Gly Ala Gly Val Ala Gly Leu Thr Thr
             5                  10                  15
GCT CTT CAA CTT CTT CGT AAA GGT CAT GAG GTT ACA ATT GTG TCC GAG     96
Ala Leu Gln Leu Leu Arg Lys Gly His Glu Val Thr Ile Val Ser Glu
                 20                  25                  30
TTT ACG CCC GGT GAT CTT AGT ATC GGA TAT ACC TCG CCT TGG GCA GGT    144
Phe Thr Pro Gly Asp Leu Ser Ile Gly Tyr Thr Ser Pro Trp Ala Gly
             35                  40                  45
GCC AAC TGG CTC ACA TTT TAC GAT GGA GGC AAG TTA GCC GAC TAC GAT    192
Ala Asn Trp Leu Thr Phe Thr Asp Gly Gly Lys Leu Ala Asp Tyr Asp
         50                  55                  60
GCC GTC TCT TAT CCT ATC TTG CGA GAG CTG GCT CGA AGC AGC CCC GAG    240
Ala Val Ser Tyr Pro Ile Leu Arg Glu Leu Ala Arg Ser Ser Pro Glu
65                  70                  75                  80
GCT GGA ATT CGA CTC ATC AAC CAA CGC TCC CAT GTT CTC AAG CGT GAT    288
Ala Gly Ile Arg Leu Ile Asn Gln Arg Ser His Val Leu Lys Arg Asp
                 85                  90                  95
CTT CCT AAA CTG GAA GGT GCC ATG TCG GCC ATC TGT CAA CGC AAC CCC    336
Leu Pro Lys Leu Glu Gly Ala Met Ser Ala Ile Cys Gln Arg Asn Pro
             100                 105                 110
TGG TTC AAA AAC ACA GTC GAT TCT TTC GAG ATT ATC GAG GAC AGG TCC    384
Trp Phe Lys Asn Thr Val Asp Ser Phe Glu Ile Ile Glu Asp Arg Ser
         115                 120                 125
AGG ATT GTC CAC GAT GAT GAG GCT TAT CTA GTC GAA TTT CGT TCC GTT    432
Arg Ile Val His Asp Asp Glu Ala Tyr Leu Val Glu Phe Arg Ser Val
     130                 135                 140
TGT ATC CAC ACC GGA GTC TAC TTG AAC TGG CTG ATG TCC CAA TGC TTA    480
Cys Ile His Thr Gly Val Tyr Leu Asn Trp Leu Met Ser Gln Cys Leu
145                 150                 155                 160
TCG CTC GGC GCC ACG GTG GTT AAA CGT CGA GTG AAC CAT ATC AAG GAT    528
Ser Leu Gly Ala Thr Val Val Lys Arg Arg Val Asn His Ile Lys Asp
                 165                 170                 175
GCC AAT TTA CTA CAC TCC TCA GGA TCA CGC CCC GAC GTG ATT GTC AAC    576
Ala Asn Leu Leu His Ser Ser Gly Ser Arg Pro Asp Val Ile Val Asn
             180                 185                 190
TGT AGT GGT CTC TTT GCC CGG TTC TTG GGA GGC GTC GAG GAC AAG AAG    624
Cys Ser Gly Leu Phe Ala Arg Phe Leu Gly Gly Val Glu Asp Lys Lys
         195                 200                 205
```

FIG. 5(b)
Prior Art

```
ATG TAC CCT ATT CGA GGA CAA GTC GTC CTT GTT CGA AAC TCT CTT CCT    672
Met Tyr Pro Ile Arg Gly Gln Val Val Leu Val Arg Asn Ser Leu Pro
    210             215                 220
TTT ATG GCC TCC TTT TCC AGC ACT CCT GAA AAA GAA AAT GAA GAC GAA    720
Phe Met Ala Ser Phe Ser Ser Thr Pro Glu Lys Glu Asn Glu Asp Glu
225             230                 235                 240
GCT CTA TAT ATC ATG ACC CGA TTC GAT GGT ACT TCT ATC ATT GGC GGT    768
Ala Leu Tyr Ile Met Thr Arg Phe Asp Gly Thr Ser Ile Ile Gly Gly
                245                 250                 255
TGT TTC CAA CCC AAC AAC TGG TCA TCC GAA CCC GAT CCT TCT CTC ACC    816
Cys Phe Gln Pro Asn Asn Trp Ser Ser Glu Pro Asp Pro Ser Leu Thr
            260                 265                 270
CAT CGA ATC CTG TCT AGA GCC CTC GAC CGA TTC CCG GAA CTG ACC AAA    864
His Arg Ile Leu Ser Arg Ala Leu Asp Arg Phe Pro Glu Leu Thr Lys
                275                 280                 285
GAT GGC CCT CTT GAC ATT GTG CGC GAA TGC GTT GGC CAC CGT CCT GGT    912
Asp Gly Pro Leu Asp Ile Val Arg Glu Cys Val Gly His Arg Pro Gly
        290                 295                 300
AGA GAG GGC GGT CCC CGA GTA GAA TTA GAG AAG ATC CCC GGC GTT GGC    960
Arg Glu Gly Gly Pro Arg Val Glu Leu Glu Lys Ile Pro Gly Val Gly
305                 310                 315                 320
TTT GTT GTC CAT AAC TAT GGT GCC GCC GGT GCT GGT TAC CAA TCC TCT   1008
Phe Val Val His Asn Tyr Gly Ala Ala Gly Ala Gly Tyr Gln Ser Ser
                325                 330                 335
TAC GGC ATG GCT GAT GAA GCT GTT TCT TAC GTC GAA AG' GCT CTT ACT   1056
Tyr Gly Met Ala Asp Glu Ala Val Ser Tyr Val Glu Arg Ala Leu Thr
                340                 345                 350
CGT CCA AAC CTT TAG                                               1071
Arg Pro Asn Leu
        355
```

TRIGONOPSIS TRANSFORMANT PRODUCING D-AMINO ACID OXIDASE

BACKGROUND OF THE INVENTION

1. Field of the Invention

The present invention relates to a *Trigonopsis variabilis* transformed with a gene capable of producing D-amino acid oxidase (hereinafter the DAO gene) and a process for transforming *Trigonopsis variabilis*. The transfomant of *Trigonopsis variabilis* is used for producing derivatives of cephalosporin C.

2. Description of Related Art

D-amino acid oxidase (hereinafter DAO) is an enzyme which catalyzes oxidative deaminination of D-amino acids. DAO is also useful to separate L-amino acids from a racemic mixture of DL-amino acids, to produce keto acids from D-amino acids and to analyze D-amino acids. A particular species of DAO produced from the yeast *Trigonopsis variabilis* (hereinafter *T. variabilis*) promotes the oxidation of not only D-amino acids but also the antibiotic cephalosporin C to produce 7-β-(5-carboxy- 5-oxopentaneamide)cephalosporanic acid, which can be reacted with $H_2O_2$ to produce 7-β-(4-carboxybutaneamide)cephalosporanic acid. Cephalosporanic acids are intermediate materials for the synthesis of cephalosporin antibiotics, which are important medical and pharmaceutical products. For example, 7-aminocephalosporanic acid (7ACA), a highly useful intermediate material, is produced by reacting these compounds with $H_2O_2$ or a cephalosporin acylase.

Past efforts of others aimed at obtaining increased amounts of DAO investigated various medium and culture conditions: F. M. Huber, *BIOTECHNOLOGY LETTERS*, 14 (3), 195–200 (1992) and Japanese Patent Publication No. 35118/1980 discloses *T. variabilis* which is activated by freezing and thawing at pH 3–4, or treating with organic solvents, surfactants and the like. Others have used conventional genetic techniques. For example, international Publication No. WO90/12110 discloses a mutant strain of *T. variabilis* which is obtained by random mutation and produces increased amount of DAO. European Patent Unexamined Publication No. 409521 discloses a problem common to all prior art efforts, namely, that *T. variabilis* has an esterase which deacetylates 3-positions in cephalosporin C, 7-β-(5-carboxy-5-oxopentaneamide)cephalospranic acid and 7-β-(4-carboxybutaneamide)cephalosporanic acid which esterase reduces the yield by deacetylating the product.

Previously, the present inventors provided a transformant of *Escherichia coli* (hereinafter *E. coli*) described in Japanese Patent Application Laid-Open No. 71180/1988, by introducing the DAO gene derived from *T. variabilis* into a host cell of *E. coli* whose cephalosporinase activity was lowered. However, the transformed *E. coli* have to be disrupted before use to recover the DAO from the cells so that their industrial scale employment is impractical. In addition, there remained a residual β-lactamase activity in the transformed *E. coli* which reduced yields.

Japanese Patent Application Laid-Open No. 200181/1990 and T. Isogai et al., *Bio/Technology*, 9, 188 (1991) disclose, respectively, transformants of *E. coli* and Achremonium chrysogenum (hereinafter A. chrysogenum) which were obtained by introducing the DAO gene derived from *Fusarium solani*. However, the use of these transformants requires taking additional steps to reduce the activity of the endogenous β-lactamase to avoid loss of the end-product.

Thus, heretofore, neither a transformant system using *T. variabilis* as a host cell nor any transformed cell which does not have endogenous β-lactamase or esterase activity has been developed.

SUMMARY OF THE INVENTION

The present invention teaches that multiple copies of a gene of interest may be stably inserted through recombinant DNA techniques into the chromosomal DNA of *T. variabilis*. More particularly, the present invention provides a novel transformant of *T. variabilis* expressing multiple copies of DAO. The *T. variabilis* of the present invention shows high DAO activity and low β-lactamase and esterase activity. Thus, the present invention may be used to produce cephalosporin C in an excellent yield. It is a further advantage of the *T. variabilis* of the present invention that they can be used for the preparation of cephalosporin C without prior mechanical disruption. Mere treatment of the cells with toluene is sufficient. Accordingly, the transformants of the present invention can be used on an industrial scale. Moreover, one skilled in the art will recognize that the transformants' desirable properties can be preserved by periodic cloning and reselection.

The present invention also provides a novel process for stably transforming *T. variabilis* and expressing a gene of interest. According to the present process, multiple copies of genes coding for enzymes and the like can be inserted into the chromosomal DNA of *T. variabilis*, expressed at high levels and remain stable without continuous selective pressure.

The present invention has also the advantage that the transformant of the invention can be inexpensively cultured on a large scale. A further advantage of the invention is its higher predictability, compared to the conventional genetic techniques of the prior art.

The present invention further provides a process for preparing 7-β-(5-carboxy-5-oxopentaneamide)cephalosporanic acid by use of DAO obtained from a transformed *T. variabilis*.

BRIEF DESCRIPTION OF THE DRAWINGS

FIG. 1 shows a N-terminal amino acid sequence SEQ. ID NO:1 for DAO.

FIG. 2 shows DNA probes (SEQ. ID NO:2–5) used for cloning the DAO gene.

FIG. 3 shows a nucleotide sequence (SEQ. ID NO:6) of an EcoRI fragment together with the N-terminal amino acid sequence (SEQ. ID NO:7) for DAO.

FIG. 5(a) and FIG. 5(b) show nucleotide sequences (SEQ ID NOS:8–9) of the DAO gene; noncoding nucleotides (AND AMINO ACID) 404–439 have been deleted from the figure.

Figure 4:
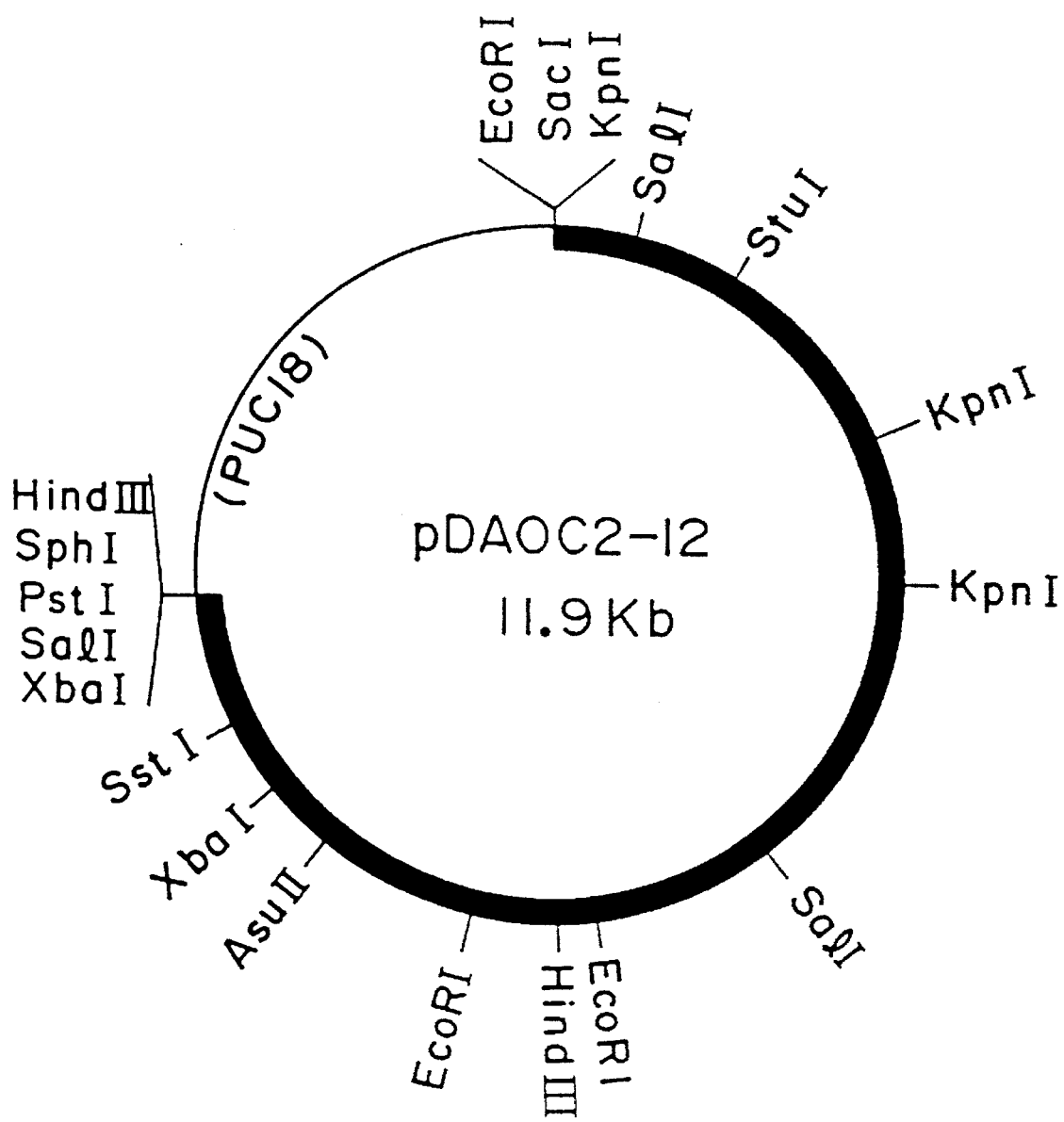
FIG. 4 is a restriction map of a plasmid pDAOC2-12.

In the figures, mark E indicates DNA derived from *T. variabilis* including the DAO gene.

DETAILED DESCRIPTION OF THE INVENTION

One aspect of the present invention is to provide *T. variabilis* which expresses recombinant DNAs encoding a DAO gene.

*T. variabilis* used in the present invention includes CBS4095 strain (Central Bureau voor Schimmelcultures), its catalase-deficient mutant KC103 which is deposited in National Institute of Bioscience and Human-Technology, Agency of Industrial Science and Technology as Deposit No. FERM BP-4359, catalase-negative mutant and other various mutants. Of these, a catalase-deficient or negative mutant is preferred because $H_2O_2$ is used as a reactant in the preparation of cephalosporin C.

Examples of DAO genes useful in the present invention include the DAO gene which has been cloned from *T. variabilis* by the present inventors, a DAO gene combined with the highly expressed promoter and terminator, and a DAO gene cloned from other species such as *F. solani* (Japanese Patent Application Laid-Open No. 200181/1990) which has been modified to be expressible in *T. variabilis*. A cDNA encoding DAO may be used as well as a genomic DAO. Of these, the DAO gene derived from *T. variabilis* is preferred because of efficiency of its promoter and codon usage.

The genome of the transformed *T. variabilis* of the present invention contains two or more of DAO genes and a marker gene; preferably, for maximal expression, between 4 and about 50 to 100 copies of the DAO genes. *T. variabilis* of the present invention exhibits low activity of the esterase due to the presence of the DAO gene. Accordingly, as the DAO copy number increases, the utility of the present invention is increased.

Representative examples of the marker gene include drug resistance genes, auxotrophic complementary genes and genes which encode enzymes such as galactosidase, whose expression is easily assayed in *T. variabilis* and drug resistance genes such as the hygromycin B resistance gene and G418 resistance gene for drugs to which *T. variabilis* is highly sensitive.

*T. variabilis* of the present invention has the same mycological characteristics as original strains except that it shows high DAO activity and low esterase activity.

*T. variabilis* of the present invention is produced according to the following outlined steps of:

(1) cloning the DAO gene from a DNA donor strain such as *T. variabilis* (Japanese Patent Application Laid-Open No. 71180/1988) by the method comprising purifying the DAO gene to determine its N-terminal amino acid sequence and isolating the DAO gene from a DNA library of the DNA donor strain with DNA oligonucleotide probes corresponding to the N-terminal amino acid sequence of the DAO;

(2) preparing a vector plasmid containing the DAO gene obtained in (1) and a fused selectable marker gene functionally linked to the promoter and 3' untranslated sequences of genes such as the DAO gene, such that it can be expressed in a host cell of *T. variabilis*, typically the marker gene is a drug resistance gene;

(3) transforming a host cell of *T. variabilis* with the vector plasmid obtained in (2) by the method comprising preparing a protoplast and introducing the vector into the host cell according alternatively to the protoplast fusion method for yeast or a physical introduction method such as electroporation and particle delivery system (BIOLISTIC™) or a chemical introduction method such as metalic ion and DMSO, all these being well know to those skilled in the art; and (4) selecting the desired transformant by culturing a population containing a transformant having the DAO gene and the marker gene in a selection medium, e.g., containing hygromycin B, cloning a resistant colony (expressing its marker gene), culturing the selected strains under non-selecting conditions, and then isolating a transformant strain which shows high synthetic activity of DAO and low synthetic activity of esterase.

A further aspect of the present invention provides a process for transforming *T. variabilis*.

The present inventors have found that a transformed *T. variabilis* capable of stably transmitting multiple copies of a desired gene into its chromosomal DNA so that it is possible to maintain the desired properties of the transformed *T. variabilis*.

In the present invention, genes encoding useful enzymes are preferably obtained from *T. variabilis* due to their higher expression. Representative examples of such genes are the DAO gene and the enantioselective NAD(P)-dependent oxidoreductase disclosed in Japanese Patent Application Laid-Open No. 117396/1990. According to the present invention, genes originated from other microorganisms, plants and animals can also be expressed.

The present invention may be successfully practiced using conventional conditions of transformation; e.g., the temperature, the culture medium, the concentration of target cells.

DESCRIPTION OF PREFERRED EMBODIMENTS

The present invention will be illustrated in more detail with reference to the following non-limiting Examples.

8 Example 19

Step1: Cloning of DAO gene
(1) Extraction of total DNA from *T. variabilis*

The totaDNA of the strain of *T. variabilis* CBSb 4095 was extracted and purified by the method of Cryer et al. (*Methods in Cell Biology*,12, 39–44 (1975), Academic Press). 40 μg of the DNA was reacted with 4 units of MobI at 37° C. for 15 min. The digested DNA was extracted an equal volume of phenol and chloroform (1:1 vol.), precipitated with ethyl alcohol and dissolved in 0.1×TE buffer (10 mM Tris-HCl buffer (pH 8.0), 1 mM EDTA). The DNA was electrophoresed on 0.7% agarose gel to recover the 6 to 9 kb fraction. 30 μg of vector plasmid pUC18 (manufactured by TAKARA SHUZO CO., LTD.) was digested with BamHI, ligated with the genomic fragments to obtain a *T. variabilis* CBS4095 genomic band library.

The ligation mixture was used to transform a selected strain of *E. coli* MC1061 obtained as follows:

A mutant strain of *E. coli* whose cephalosporinase activity has been lowered was prepared by the following procedures. *E. coli* MC1061 (obtained from Dr. Malcom Casadaban, University of Chicago, U.S.A.; see Casadaban, *J. Mol. Biol*, 138, 179–207 (1980)) was treated with N-methyl-N'-nitro-Nnitrosoguanidine and colonies showing high sensitivity to cephalosporin C were selected. Of these, the strains whose cephalosporinase activity has been lowered were further selected and separated. One, MB65, which was used to express the pUC18 band library, is deposited in National Institute of Bioscience and Human-Technology, Agency of Industrial Science and Technology as Deposit No. FERM BP-4360.

(2) Determination of N-terminal amino acid sequence of DAO 60 g of wet cells of *T. variabilis* CBSb 4095 were suspended in 60 ml of 0.1M phosphate buffer (pH 7.5) and subjected to ultrasonication for 5 min. Then, the suspension was centrifuged to obtain a supernatant. The supernatant was subjected to ammonium sulfate precipitation to recover 20 to 60% of the ammonium sulfate fractions of the supernatant. The recovered fractions were dialyzed against 0.05M phosphate buffer (pH 7.5), then column chromatographed with DEAE-Sepharose CL-6B column (manufactured by Pharmacia LKB Biotechnology AB; column scale 200 ml, NaCl 0→0.5M gradient) to obtain an active fraction. The fraction was dialyzed against 0.05M phosphate buffer (pH 7.5), then column chromatographed with HPLC DEAE-5PW (manufactured by TOSO CORPORATION; 21.5 mm×150 mm, NaCl 0→0.5M gradient) to obtain an active fraction. The resultant fraction was concentrated by using Centriprep (manufactured by AMICON Inc.), then the concentrate was subjected to HPLC with PROTEIN COLUMN 300 (manufactured by Millipore CORPORATION; 7.8 mm×300 mm, aqueous solution containing 0.1M KPB solution (pH 7.0) and 0.2M NaCl) to obtain purified DAO, which was given a single bound in SDS-PAGE.

The N-terminal amino acid sequence of the purified DAO was analyzed by the method of Hunkapiller et al. (*Science*, 219, 650–659 (1983)) to determine the amino acid sequence from the N-terminal to the 41st amino acid. The resultant amino acid sequence (SEQ. ID NO:1) is shown in FIG. 1.

(3) Preparation of DNA probe

Degenerate oligonucleotide probes encoding the two amino acid sequences (See SEQ. ID NO:1) underlined in FIG. 1 were synthesized by using a DNA synthesizer model 380-A (manufactured by Applied Biosystems Inc.). The oligonucleotide sequences (SEQ. ID NOS:2–5) of probes DAO-1, DAO-2, DAO-3 and DAO-4 are shown in FIG. 2.

(4) Screening and identification of the DAO clone

The DNA probes obtained in (3) were labeled with T4polynucleotide-kinase and $\gamma$-$^{32}$P-ATP by the method of Inglia et al. (Inglia et al., *Nucleic Acids Res.*, 9, 1627–1642 (1982)). *E. coli* obtained in (1) were cultured on L-broth agar medium containing 50 µg/ml of Ampicillin to form colonies. The resultant colonies were transferred to a Whatman 541 filter paper by using a replica method, and the replicated colonies were lysed by Lysozyme. The DNA was denatured with alkali, neutralized with HCl, and hybridized with labeled probes DAO-1 and DAO-2, respectively. The hybridization was performed with 6×SSC solution containing 0.15M NaCl and 0.015M sodium citrate (pH 7.5), 0.5% NONIDET P-40 (manufactured by SIGUMA CHEMICAL COMPANY) and probes DAO-1 or DAO-2 (about 2×10$^5$ cpm/ml) at 44° C. for 1.5 hrs. The filter paper was washed with 6×SSC twice at room temperature and once at 44°0 C. Then, the filter paper was dried and autoradiographed at −80° C. for 3 hrs.

40 positive colonies were picked and expanded in liquid culture. Plasmid DNA was prepared from the strains by the method of Birnboim et al. (*Nucleic Acids Res.*, 7, 1513–1523 (1979)). The resultant DNA was denatured by conventional methods, spotted on a nitrocellulose filter, and then hybridized with the each DNA probe. Each hybridization was performed with 6×SSC solution, 10 ×Denhardt solution containing 0.02% of Ficoll, 0.02% of polyvinyl pyrrolidone and 0.02% of bovine serum albumine and a solution containing each labeled DNA probe at 44° C. for 1 hr. for probes DAO-1 and DAO-2, and at 40° C. for 1 hr. for probes DAO-3 and DAO-4. The nitrocellulose filter was washed with 6×SSC at room temperature, and further washed with 6×SSC at 44° C. for probes DAO-1and DAO-2 and at 40° C. for probes DAO-3 and DAO-4. Then, the filter was dried and autoradiographed at −80° C. for 3 hrs. 6 colonies positive for probes DAO-1 or DAO-2 and also for DAO-3 or DAO-4 were found. Upon further analysis, a clone having a 0.6 kb EcoRI fragment strongly positive for probes DAO-2 and DAO-3 or DAO-4, was found and named plasmid pDAOC2-12.

(b 5) Identification of DAO clone and determination of its DNA sequence

The nucleotide sequence of the 0.6 kb DNA fragment was determined by the method of Sanger et al. (*Proc. Natl. Acad. Sci. U.S.A.*, 74, 5463–5467 (1977)), and found to include the N-termina 83 residues of the DAO gene (SEQ. ID NO:6) shown in FIG. 3. A restriction map of plasmid pDAOC2-12 is shown in FIG. 4. Upon further sequence analysis the plasmid pDAOC2 -12 proved to encode for a protein (SEQ ID NO:9) composed of 355 amino acids shown in. FIGS. 5(*a*) and (*b*). The presence of the TAG stop codon at 1069indicates that the pDAOC-12 insert is a ful length copy of the DAO gene.

(6) Modification of DAO gene

A BanI site was inserted into an intron according to the following process.

40 µg of plasmid pDAOC-12 was digested with EcoRI and HindIII to obtain a 0.45 kb fragment. The purified fragment (0.8 µg) was reacted with dATP, dGTP, dCTP and TTP which having a fina concentration of 0.33 mM, respectively, and 5 units of DNA polymerase Klenow fragments in 30 µl of a reaction solution containing 10 mM Tris-HCl (pH 7.5), 10 mM MgCl$_2$, 1mM dithiothreito and 50mM NaCb at 30° C. for 20min. to obtain blunt ends. About 0.2 µg of the purified DNA fragments was reacted with BamHI linker (0.0175 O.D.) and 1 unit of T4 DNA ligase in 20 µl of a reaction solution containing 50 mM Tris-HC (pH 7.5), 10 mM MgCl$_2$, 0.5 mM ATP and 5 mM dithiothreito at 15° C. overnight. The resultant DNA fragments were recovered, purified, then digested with EcoRI and BamHI to obtain EcoRI-BamHI fragments. A double-stranded DNA of Mb13 mp18 phage (manufactured by TAKARA SHUZO CO., LTD.) was digested with EcoRI and BamHI, then the digested M13mp18 phage (SEQ. ID NO:9) and the above-obtained EcoRI-BamHI fragments were ligated with T4 ligase to produce a M13M2-12-7 phage containing a part of the DAO gene.

Figure 6:
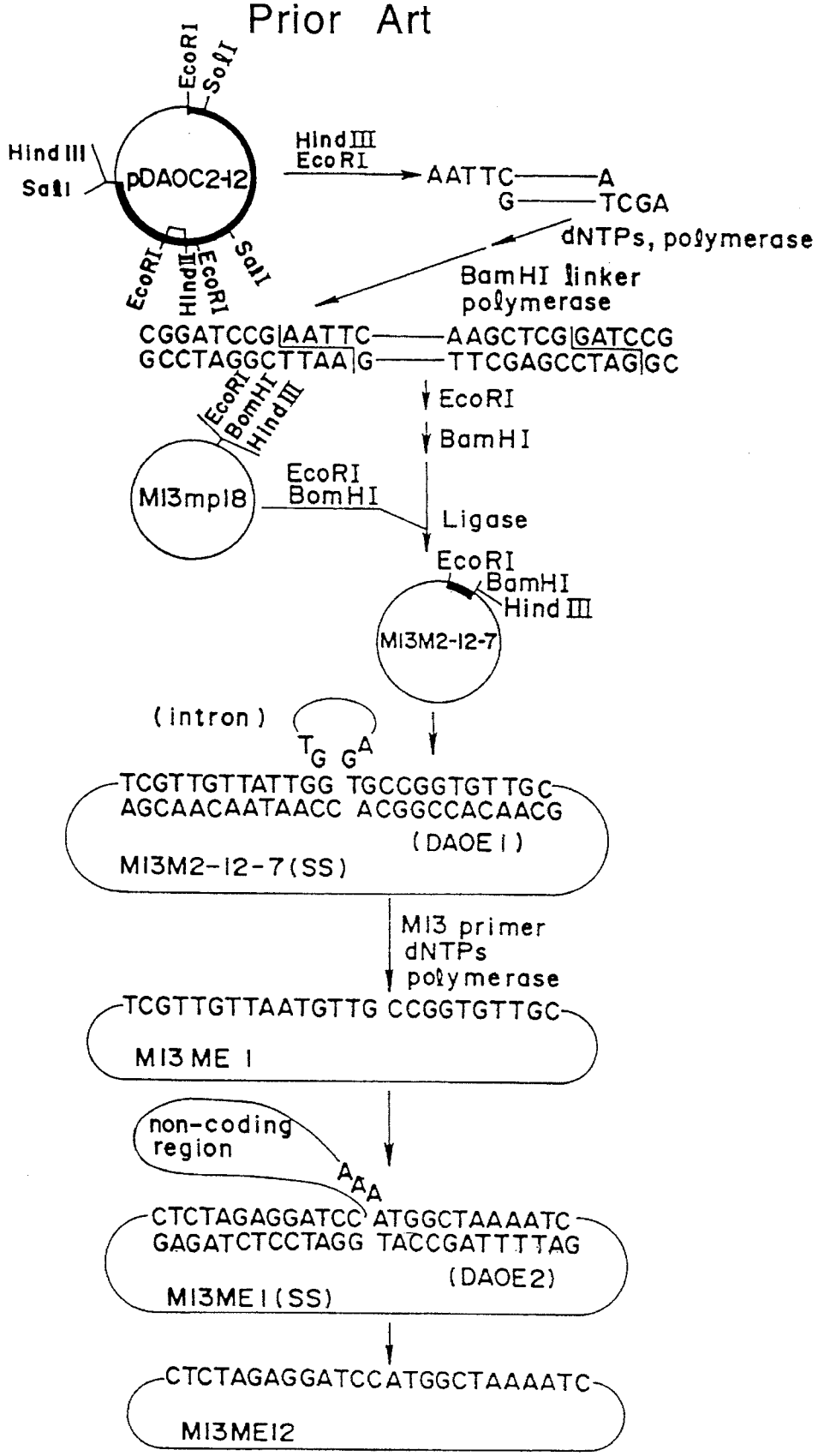
FIG. 6 is a diagram showing the preparation of plasmid 13ME1 (SEQ.ID NOS:10–15 having a part of the DAO gene having a BanI site in an intron.
Figure 7:
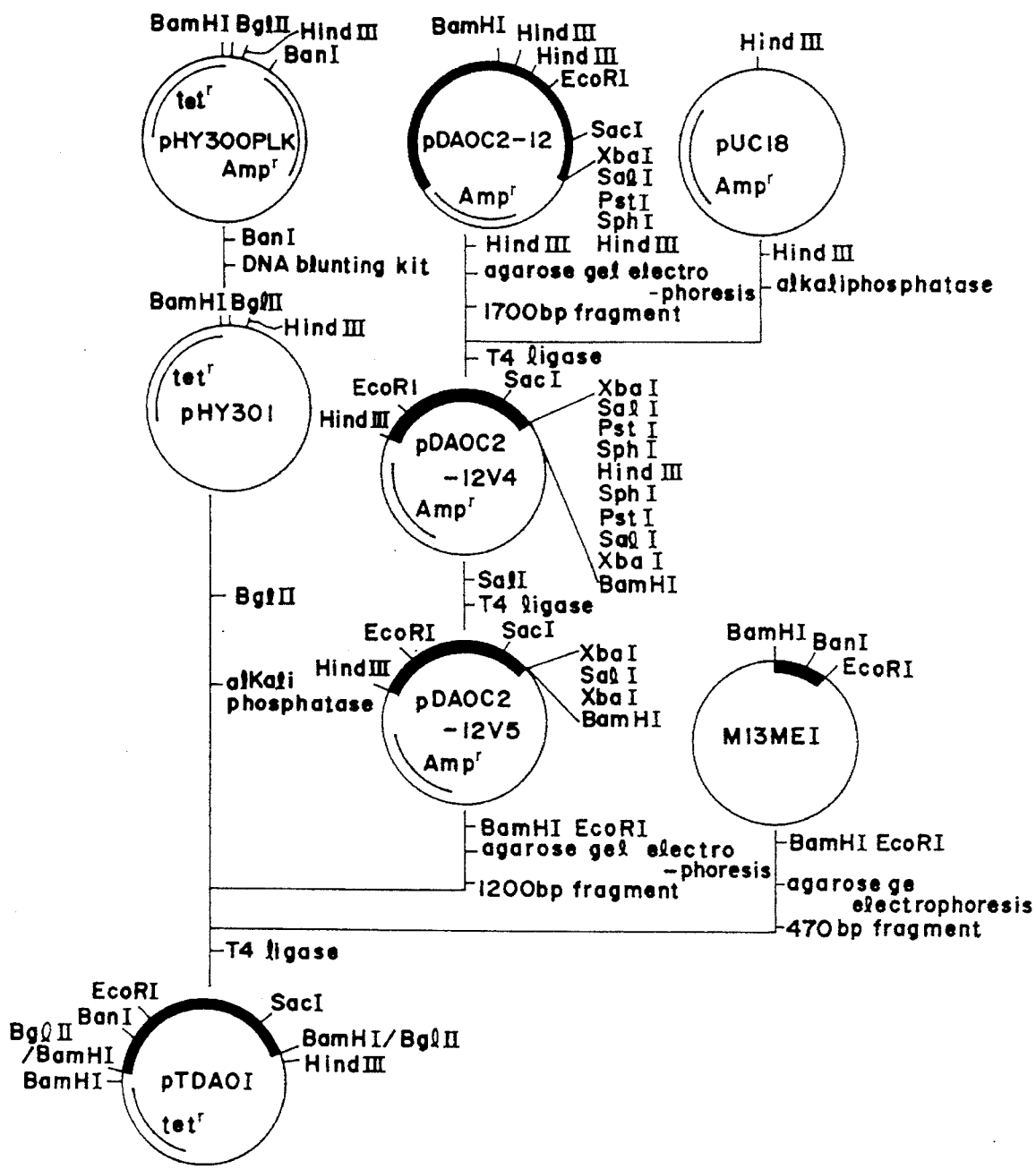
FIG. 7 is a diagram showing the preparation of plasmid pTDO1 having the DAO gene having BanI site in an intron.
Figure 8:
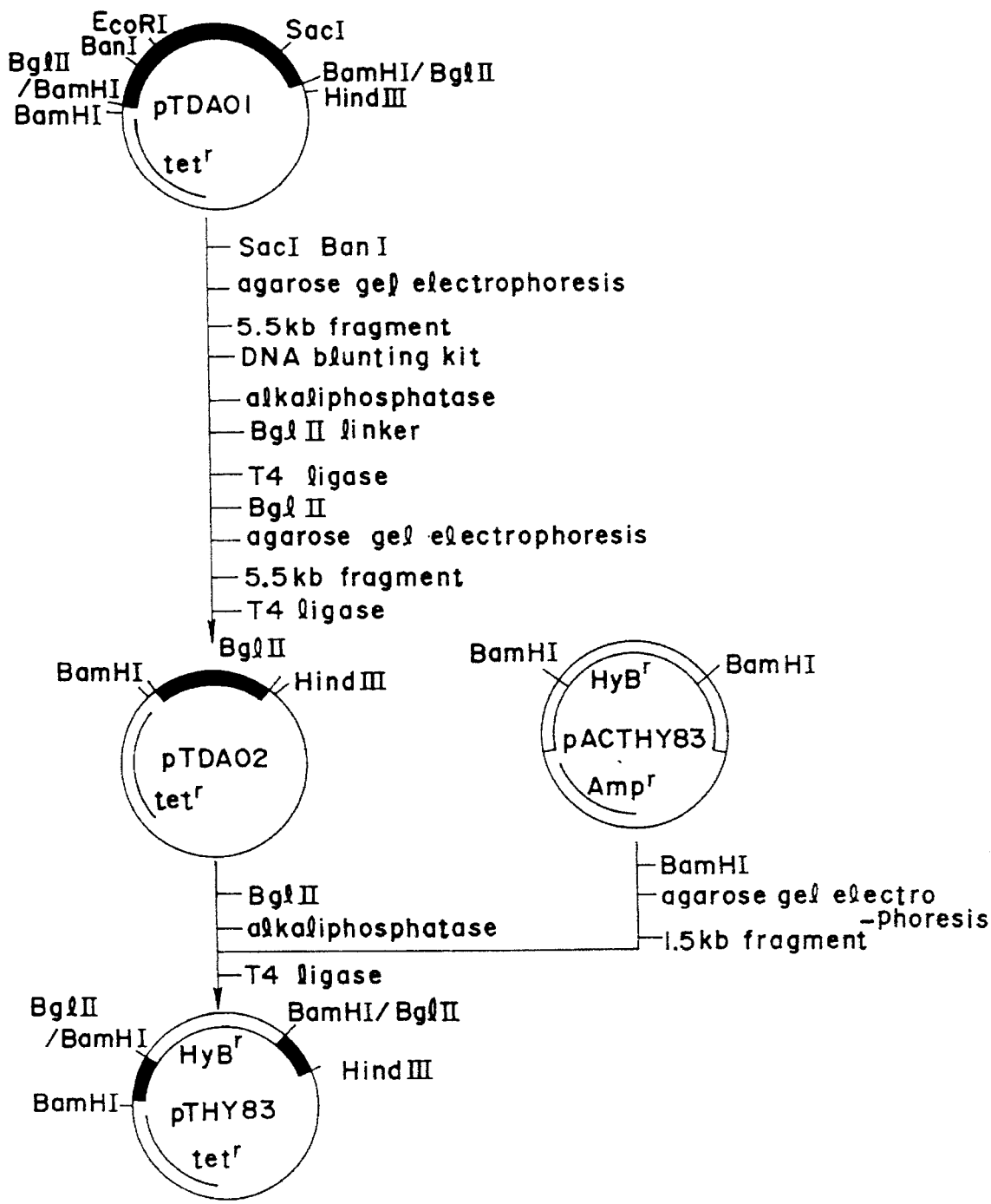
FIG. 8 is a diagram showing the preparation of plasmid pTHY83 having a hygromycin B resistance gene.
Figure 9:
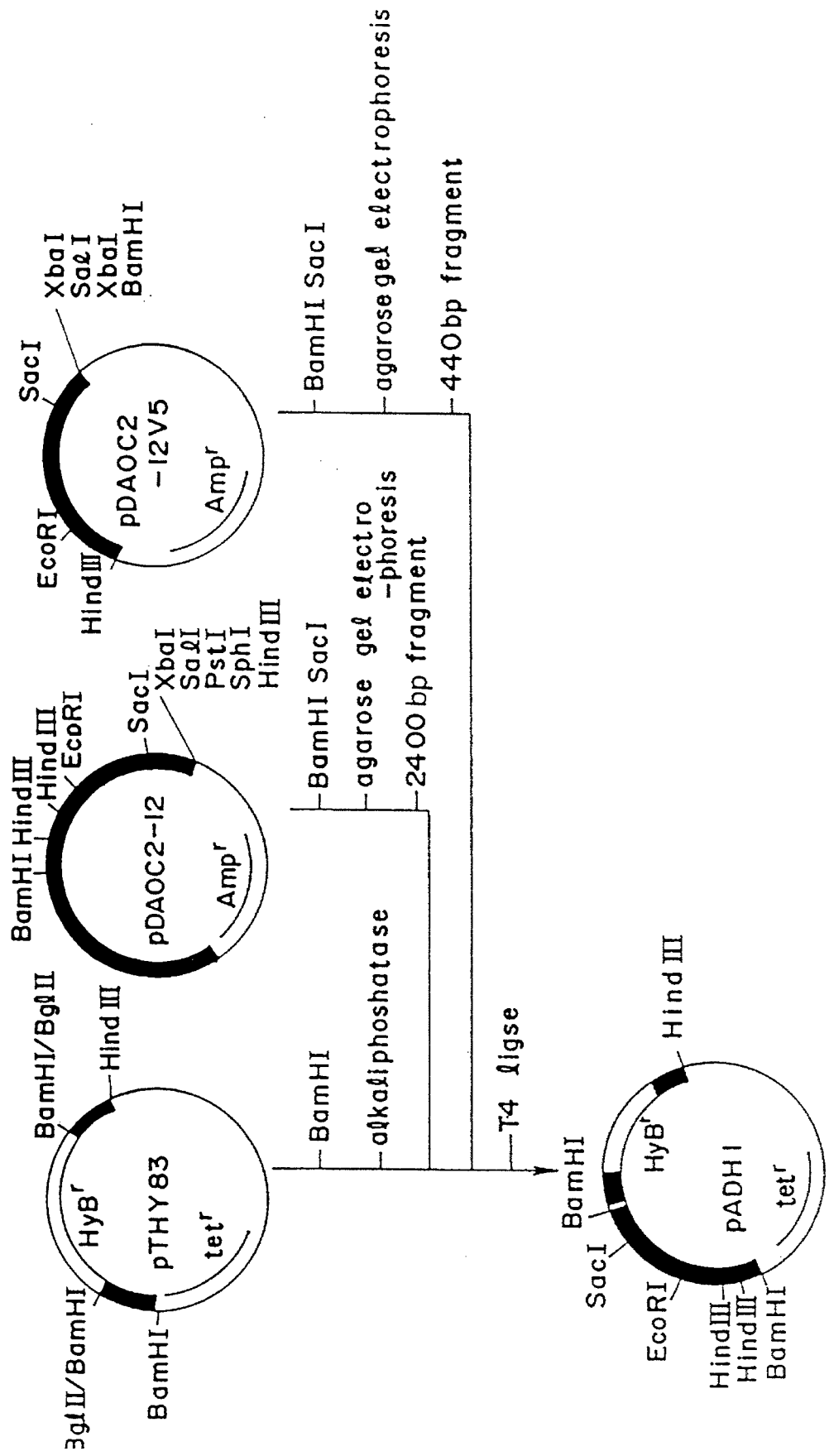
FIG. 9 is a diagram showing the preparation of plasmid pADH1 which can be used to introduce the DAO gene.

For the purpose of insertion of a BanI site into an intron, an oligonucleotide complementary (SEQ. ID NO:12) to the nucleotide sequence combining the head and end of the intron, as shown in FIG. 6, was produced and named DAOE1. 25 pmole of DAOE1 and 10 pmole of Mb 13 primer M1(manufactured by TAKARA SHUZO CO., LTD.) were phosphorylated with T4polynucleotide kinase, followed by addition of about 0.5 pmole of a single-stranded M13M2-12-7 phage prepared by the method of Messing (*Methods Enzymol.*, 101, 20–78 (1983)). Then, the resultant was heated at 95° C. for 5min. and allowed to stand until the reaction mixture was cooled to room temperature. Subsequently, the resultant mixture was reacted with 0.4 mM dATP, 0.4 mM dGTP, 0.4 mM dCTP and 0.4 mM TTP, 0.4 mMATP, 5 units of DNA polymerase Klenow fragment and 2units of T4 DNA ligase in 50 µl of reaction solution containing 7 mM Tris-HCl (pH 7.5), 7 mM MgCl$_2$, 7 mM NaCb and 14 mM dithiothreito at 37° C. for 30 min. 5 µl of 0.5M EDTA was added and the reaction was stopped. *E. coli* JM105 placed in RIKEN (the Institute of Physical and Chemical Research) DNA Bank as RDB 103 strain was infected with the resultant phage suspension according to the abovementioned Messing method to form plaques. The plaques were hybridized with $_{32}$ P-labeled DAOE1 according to plaque hybridization method (Science, 196, 180 –182 (1977)). The positive plaque was repeatedly purified by the above-described hybridization process. Then, a phage in the purified plaque was subjected to liquid culture according to conventional methods to obtain a single-stranded DNA was analyzed. As expected, it was found that the nucleotide sequence included a DNA fragment which was derived from *T. variabilis*CBS4095 having a BanI site and did not have an intron. The phage was named M13ME1 phage. (SEQ. ID NO:13)

Step 2: Preparation of marker gene for transformation
(1) Deletion of BanI site in pHY300PLK A BanI site, which might disturb the construction of plasmids, in pHY300PLK (manufactured by TAKARA SHUZO CO., LTD.) was deleted according to the following process. 3 µg of plasmid pHY300PLK was digested with BanI, then further digested by using DNA blunting kit (manufactured by TAKARA SHUZO CO., LTD.) to obtain blunt ends, and self-ligated. The resultant plasmid was introduced into *E. coli MB65* (FERM BP-4360) and cultured on L-broth agar medium containing 10 µg/m of tetracycline to select transformants. Then, a plasmid without the BanI site was prepared by the method of the above-mentioned Birnboim et al. and named pHY301.

(2) Preparation of plasmid pTDAO1

A plasmid pTDAO1having the DAO gene of *T. variabilis* without an intron on pHY301 was prepared according to the following process. The 1700 kb fragment obtained by digesting plasmid pDAOC2-12 with HindIII was purified by agarose gel electrophoresis and recovered. 200 ng of the recovered fragment was mixed with 1 µg of plasmid pUC18 which was digested with HindIII and treated with alkalinphosphatase and ligated with T4 DNA ligase to obtain plasmid pDAOC2-12V4.

In order to delete the palindrome, the pDAOC2-12V4 was digested with SalI and self-ligated with T4 DNA ligase to obtain plasmid pDAOC2-12V5. The plasmid pDAOC2-12 V5 was digested with BamHI and EcoRI to obtain the 1200 bp fragment. The 1200 bp fragment was purified by agarose ge electrophoresis. Double-stranded M13ME1 was digested with BamHI and EcoRI to obtain the 470bp fragment. The 470 bp fragment was also purified by agarose gel electrophoresis. 200 ng of each resultant fragment and 1 µg of plasmid pHY301 digested with BglII and treated with an alkalinphosphatase were mixed and ligated with T4DNA ligase to obtain plasmid pTDAO1.

(3) Preparation of plasmid pTDAO2

Plasmid pTDAO2having the *T. variabilis* DAO promoter and 3' untranslated sequence was prepared according to the following process. Plasmid pTDAO1 was digested with SacI and BanI to obtain the 5.5 kb fragment. The 5.5 kb fragment was purified by agarose gel electrophoresis. 1 µg of the fragment was digested with DNA blunting kit (manufactured by TAKARA SHUZO CO., LTD.) to obtain blunt ends and treated with an alkalinphosphatase. Then, the resultant fragment and 300 ng of BglII linker (8 bp, manufactured by TAKARA SHUZO CO., LTD.) were mixed, ligated with T4 DNA ligase, digested with BglII and purified by agarose ge electrophoresis to recover the 5.5 kb fragment. The fragment was self-ligated with T4 DNA ligase to obtain plasmid pTDAO2.

(4) Preparation of plasmid pTHY83

Plasmid pTHY83 was prepared to express hygromycin B resistance genes under control of the pTDAO2 promoter and 3' untranslated sequence. 1 µg of plasmid pTDAO2 obtained in (3) was digested with BglII, then treated with an alkalinphosphatase. Plasmid pACTHY83 having the hygromycin B resistance genes (constructed according to the description of EP-A-450758) was digested with BamHI to obtain the 1.5 kb fragment. 200 ng of a 1.5 kb fragment was purified by an agarose ge electrophoresis. The resultant fragments were mixed and ligated with T4 DNA ligase to obtain plasmid pTHY83.

Step 3: Preparation of transformant of *T. variabilis*
(1) Preparation of protoplast

*T. variabilis* CBS4095 strain was cultured on YEPD medium containing 10 g/l of yeast extract, 20 g/l of peptone and 20 g/l of glucose for 30 hrs. A 1.5 m harvest was suspended in 1.5 m of a reduction buffer (0.05% mercuptoethanol, 10 mM Tris-HCl, pH 7.5), incubated at 30° C. for 15 min., and transferred to 2 ml of A-buffer (0.6M sucrose, 2% MgSO$_4$, 50 mM Tris-HCl, pH 8.0) containing NOVOZYM™ (manufactured by NOVO Biolabs.), and incubated at 30° C. for 3 hrs. Then, the protoplasts were collected and washed with A-buffer.

(2) Introduction of the plasmid pTHY83 by protoplast fusion

The protoplasts obtained above was suspended in 80µ of B-buffer (0.75M sucrose, 50 mM CaCl$_2$, 10 mM Tris-HCl pH 8.2). 10 µg of pTHY83 was added in 20 µl and incubated at 30° C. for 3 min. Then, 900 µl of C-buffer (0.6M sucrose, 50 mM CaCl$_2$, 38% polyethylene glycol, 10 mM Tris-HCl, pH 8.2) was added and the mixture incubated at 30° C. for a further 30 min. Then, the protoplasts were collected, washed with A-buffer and recollected.

Step 4: Screening of transformants

The fused protoplasts were suspended in 1.5 ml of A-buffer and 300 µl was spread on each of five plates containing 12.5 ml of a protoplast regeneration medium including 10 g/l of yeast extract, 20 g/l of peptone, 20 g/l of glucose, 0.6M sucrose, 3 g/l of DL-methionine and 25 g/l of agar, and incubated bated 30° C. for 12 hrs. Then, 7.5 ml of the regeneration medium containing 4 mg of hygromycin B was laminated on the plates and further incubated at 30° C. for 1 to 2 weeks. As a result, 13 hygromycin B resistant colonies (hereinafter HYB transformants) were obtained. Although the same transformation as described above was conducted using plasmid pHY300 PLK as a control plasmid, HYB transformants could not be obtained.

8 Example 2 9

Using a catalase-deficient mutant of the *T. variabilis* KC103 strain (FERM BP-4359) as a host cell, the same transformation protocol was used to obtain 10 HYB transformants. Again HYB transformants could not be obtained with pHY300 PLK.

8 Example 3 9

Preparation of *T. variabilis* transformed with the DAO gene Step 1 : Preparation of plasmid pADH1

Plasmid pADH1 having the DAO gene and the hygromycin B resistance gene as a marker gene was prepared according to the following process. Plasmids pDAOC2 -12V5 and pDAOC2 -12 were digested with BamHI and SacI to obtain 440 bp and 2.4 kb fragments respectively. 1 µg of plasmid pTHY83 was digested with BamHI and treated with alkalinephosphatase, mixed with 100 ng of the 400 bp fragment and 200 ng of the 2.4 kb fragment, and ligated with T4 DNA ligase to obtain plasmid pADH1. Step 2: Transformation of T. variabilis with plasmid pADH1

Using T. variabilis CBS4095 strain as a host cell and the plasmid pADH1, the same transformation as described in Example 1 was conducted to obtain 8HYB transformants.
Step 3: Measurement of DAO activity One inoculation loop of the HYB transformants was planted in 3 ml of YEPD liquid medium containing 50 μg/ml of hygromycin B and incubated at 28° C. for 38 hrs. 6 ml of 30 % glycerol was added to the culture medium and left at −70° C. 1 ml of preservation solution was used to inoculate a 500 ml flask containing 50 ml of fermentation medium (glucose 2.5%, DL-methionine 0.3%, $MgSO_4$ 0.1%, $KH_2PO_4$ 0.4%, C.S.L. 6%, Shin-Etsu Silicone KM-72 (manufactured by Shin-Etsu Chemical Co., Ltd.) 0.5%, pH 6.5), and incubated at 28° C. for 40 hrs. Then, 2 ml of 50% glucose was added to the culture medium and incubated for 20 hrs. 500 μl of the culture liquid was transferred into a 2 ml of tube (manufactured by Eppendorf Inc.). Then, 15 μl of toluene was added to the culture liquid, stirred with a microtube mixer (manufactured by TOMY-SEIKO Co., Ltd., speed 10) at room temperature for 2 hrs. to collect cells. The collected cells were washed with 1 ml of water and suspended in 500 μl of-water to obtain a suspension of permeabilized cells treated with toluene. 10 μl of this suspension was mixed with 90 μl of a reaction buffer containing 11 mg/ml of Cepharosporin C and 110 mM of Tris-HCl (pH 7.5) in a test tube. Subsequently, the resultant mixture was stirred with a shaker (240 r.p.m.) at 25° C. for 10 min., and mixed with the mixture of a stopper (17 mM NaCl, 13.3% acetic acid) having the same volume as the resultant mixture to stop the reaction. The resultant solution was subjected to HPLC (inertsil-ODS-2 column manufactured by GL Science Inc., 5% acetomitril-3% sodium acetate solution, flow rate: 1 ml/min, detector: λ254 nm) to determine a quantity of the produced 7-β-(5-carboxy-5-oxopentaneamide)cephalosporanic acid and 7-β-(4-carboxybutaneamide)cephalosporanic acid. The amount necessary to produce 1 μmole of each compound per a minute is defined as one unit of DAO activity and the activity per 1 ml of culture medium is shown in Table 1. Some of the resultant strains had significantly enhanced the DAO activity than that of CBS4095 strain.
Step 4: Measurement of esterase activity Activity of an esterase whose substrate is 7-β-(4-carboxybutaneamide)cephalosporanic acid was measured according to the follow process. 100 μl of the suspension of the permeabilized cells treated with toluene, which was obtained in Step 3, mixed with 400 μl of an esterase reaction buffer (2.5 mg/ml 7-β-(4-carboxybutaneamide)cephalosporanic acid, 250 mM Tris-HCl pH 7.5), incubated at 25° C. for 30 min. and further mixed with 500 μl of methyl alcohol to stop the reaction. The reaction solution was subjected to HPLC (zorbax BP-$NH_2$ column (manufactured by Sumika Chemical Analysis Service Ltd.), 12% acetonitril-8% acetic acid-4% methyl alcohol, flow rate: 1.8 ml/min, detector: λ254 nm) to determine a quantity of the produced deacethyl-7-β-(4-carboxy-butaneamido)cephalosporanic acid. The amount necessary to produce 1 μmole of the compound per a minute is defined as one unit of the esterase activity, and the activity per 1 ml of culture medium is shown in Table 2. The esterase activity of some strains was meaningfully reduced compared to that of CBS4095 strain.

The esterase activity of the transformants obtained by introducing a plasmid having a part of the DAO gene in Examples 1 and 2 were also measured by the same method as described above and the results are shown in Table 2. Their activity was reduced compared to CBS4095 strain and KC103 strain. Thus, the reduction of the esterase activity occured irrespective of the increase of the DAO activity.

8 Example 4 9

Using T. variabilis KC103 strain (FERM BP-4359) as a host cell and plasmid pADH1, the same transformation as described in Example 1 was conducted to obtain 9 HYB transformants.

The DAO activities of the transformants were measured by the same method as described in Step 3in Example 3 and the results are shown in Table 1. Some transformants had enhanced DAO activity compared to KC103 strain.

Esterase activity of the transformants were measured by the same method as described in Step 4 in Example 3 and the result is shown in Table 2. Some had meaningfully reduced esterase activity compared to KC103 strain.

The transformants were cultured for 60 hrs. in broth without selective pressure. DNA was extracted according to the method of Cryer et al., supra., and 5 μg of the total DNA was digested with HindIII. The digest was sized, blotted and probed with the 800 bp EcoRI-Sac fragment of pDAOC2-12V4. The blot showed that the transformants contained a 4.0 kb HindIII derived from plasmid pADH1 indicating tandem integration, weak bands showing random integration, as well as the background 3.2 kb band found in untransformed DNA of KC103 strain. A ratio of the radioactive intensity of the 4.0 kb band to that of the 3.2 kb band was measured by Bioimage-analyzer BSA2000 (manufactured by Fuji Photo Film Co., Ltd.) and the result is shown in Table 3. It was confirmed that the multiple copies of the DAO genes were present in the chromosomal DNA.

TABLE 1

|  | Strain | DAO activity (unit/ml) |
| --- | --- | --- |
| Example 3 | pADH1/CBS4095 - 1 | 8.79 |
|  | - 2 | 3.50 |
|  | - 3 | 0.82 |
|  | - 4 | 0.80 |
|  | - 5 | 1.21 |
|  | - 6 | 7.36 |
|  | - 7 | 0.83 |
|  | - 8 | 0.79 |
| Control | CBS4095 (parent) | 0.77 |
| Example 4 | pADH1/KC103 - 1 | 1.76 |
|  | - 2 | 4.52 |
|  | - 3 | 1.60 |
|  | - 4 | 4.59 |
|  | - 5 | 5.12 |
|  | - 6 | 0.82 |
|  | - 7 | 1.78 |
|  | - 8 | 2.70 |
|  | - 9 | 2.93 |
| Control | KC103 (parent) | 0.90 |

TABLE 2

|  | Strain | Esterase activity (unit/ml) |
| --- | --- | --- |
| Example 1 | pTHY83/CBS4095 - 1 | 0.018 |
|  | - 2 | 0.016 |
|  | - 3 | 0.017 |
|  | - 4 | 0.017 |
| Example 2 | pTHY83/KC103 - 1 | 0.021 |
|  | - 2 | 0.030 |
|  | - 3 | 0.032 |
|  | - 4 | 0.014 |
| Example 3 | pADH1/CBS4095 - 1 | 0.010 |

TABLE 2-continued

| | Strain | Esterase activity (unit/ml) |
|---|---|---|
| | - 2 | 0.015 |
| | - 3 | 0.021 |
| | - 4 | 0.022 |
| | - 5 | 0.022 |
| | - 6 | 0.012 |
| | - 7 | 0.016 |
| | - 8 | 0.017 |
| Example 4 | pADH1/KC103 - 1 | 0.047 |
| | - 2 | 0.030 |
| | - 3 | 0.041 |
| | - 4 | 0.039 |
| | - 5 | 0.029 |
| | - 6 | 0.031 |
| | - 7 | 0.054 |
| | - 8 | 0.047 |
| | - 9 | 0.049 |
| Control | CBS4095 (parent) | 0.023 |
| | KC103 (parent) | 0.099 |

TABLE 3

| | Strain | Ratio of intensity of radioactivity (4.0 kb/3.2 kb) |
|---|---|---|
| Example 4 | pADH1/KC103 - 1 | 10.5 |
| | - 2 | 10.5 |
| | - 3 | 6.1 |
| | - 4 | 4.1 |
| | - 5 | 4.5 |
| | - 6 | 0 |
| | - 7 | 0.3 |
| | - 8 | 9.4 |
| | - 9 | 23.5 |
| Control | KC103 (parent) | 0 |

What is claimed is:

1. A *Trigonopsis variabilis* transformed with a recombinant DNA comprising a D-amino acid oxidase gene which is expressed in the transformed *Trigonopsis variabilis*, wherein the transformed *Trigonopsis variabilis* has two or more copies of D-amino acid oxidose gene and a marker gene in the chromosomal DNA of the *Trigonopsis variabilis*, and the transformed *Trigonopsis variabilis* possesses higher D-amino oxidase acid activity and lower esterase activity relative to an untransformed parent strain.

2. The *Trigonopsis variabilis* according to claim 1, that is a catalase-deficient mutant.

3. The *Trigonopsis variabilis* according to claim 1, wherein the transformed *Trigonopsis variabilis* is characterized by a D-amino acid oxidase/esterase activity ratio of 3 to 26 times that of a parent strain.

4. The *Trigonopsis variabilis* according to claim 1, wherein the transformed *Trigonopsis variabilis* is characterized by a D-amino acid oxidase/esterase activity ratio of 12 to 26 times that of a parent strain.

5. The *Trigonopsis variabilis* according to claim 1, wherein the transformed *Trigonopsis variabilis* is characterized by a D-amino acid oxidase/esterase activity ratio of 18 to 26 times that of a parent strain.

6. The *Trigonopsis variabilis* according to claim 1, wherein the transformed *Trigonopsis variabilis* is a CBS4095 strain.

7. The *Trigonopsis variabilis* according to claim 1, wherein the transformed *Trigonopsis variabilis* is a KC103 strain.

8. The *Trigonopsis variabilis* according to claim 1, wherein the transformed *Trigonopsis variabilis* is transformed by plasmid pADH1.

* * * * *

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
      ( A ) LENGTH: 41 amino acids
      ( B ) TYPE: amino acid
      ( C ) STRANDEDNESS: single
      ( D ) TOPOLOGY: unknown ( i i ) MOLECULE TYPE: peptide ( x i ) SEQUENCE DESCRIPTION: SEQ ID NO:1:

```
Ala Lys Ile Val Val Ile Gly Ala Gly Val Ala Gly Leu Thr Thr Ala
1               5                   10                  15

Leu Gln Leu Leu Arg Lys Gly His Glu Val Thr Ile Val Ser Glu Phe
            20                  25                  30

Thr Pro Gly Asp Leu Ser Ile Gly Tyr
            35                  40
```

( 2 ) INFORMATION FOR SEQ ID NO:2:

( i ) SEQUENCE CHARACTERISTICS:
      ( A ) LENGTH: 16 base pairs
      ( B ) TYPE: nucleic acid
      ( C ) STRANDEDNESS: single
      ( D ) TOPOLOGY: unknown ( i i ) MOLECULE TYPE: DNA ( x i ) SEQUENCE DESCRIPTION: SEQ ID NO:2:

GNAARGGYCA YGARGT  16

( 2 ) INFORMATION FOR SEQ ID NO:3:

( i ) SEQUENCE CHARACTERISTICS:
      ( A ) LENGTH: 16 base pairs
      ( B ) TYPE: nucleic acid
      ( C ) STRANDEDNESS: single
      ( D ) TOPOLOGY: unknown ( i i ) MOLECULE TYPE: DNA ( x i ) SEQUENCE DESCRIPTION: SEQ ID NO:3:

GNAARGGRCA YGARGT 16

( 2 ) INFORMATION FOR SEQ ID NO:4:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: unknown ( i i ) MOLECULE TYPE: DNA ( x i ) SEQUENCE DESCRIPTION: SEQ ID NO:4:

GARTTYACYC CNGG 14

( 2 ) INFORMATION FOR SEQ ID NO:5:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: unknown ( i i ) MOLECULE TYPE: DNA ( x i ) SEQUENCE DESCRIPTION: SEQ ID NO:5:

GARTTYACRC CNGG 14

( 2 ) INFORMATION FOR SEQ ID NO:6:

( i ) SEQUENCE CHARACTERISTICS:
        ( A ) LENGTH: 666 base pairs
        ( B ) TYPE: nucleic acid
        ( C ) STRANDEDNESS: double
        ( D ) TOPOLOGY: unknown ( i i ) MOLECULE TYPE: DNA ( i x ) FEATURE:
        ( A ) NAME/KEY: CDS
        ( B ) LOCATION: join(381..404, 441..665)

( x i ) SEQUENCE DESCRIPTION: SEQ ID NO:6:

```
GAATTCAGAC ATGGCAGAAT TAACGGCCA CTACAGTTGG CCGTTCGTAA ACGAGACAAG      60

TGACTCANGG CAGCACCGTC TCAGTCCACC GGTCTAAAGC ATTGGTGCCA GATGAATTTG     120

GAAACTGTCA CCTTATAGAA TTACTTTTGG ATAGTTTTTG TAAGGCTGGA GACTTGTAAG    180

CCTGACTCAT TGACTCATCG GCGAAAGCTT CCTATCTTGG AGCTAAGATC GCCTGATCGT    240

TTTGCCCTAC TTATCTTGGT TGCATGAGTT GGCCGGTCAG AGCCGCATTC TAGCCAAAGG    300

GTTATAGCGT TACACTCTTG ATAGGCAAAT CCGTGCTCGG ATTATATATA AGGCAAAAGT    360

CGATTCAACG GATCAATAAA ATG GCT AAA ATC GTT GTT ATT GGG TAAGTGCCTG    414
                         Met Ala Lys Ile Val Val Ile Gly
                          1               5

ATACCAGACG GCTGACATTG TTTAGT GCC GGT GTT GCC GGT TTA ACT ACA GCT   467
                            Ala Gly Val Ala Gly Leu Thr Thr Ala
                                      10                  15

CTT CAA CTT CTT CGT AAA GGT CAT GAG GTT ACA ATT GTG TCC GAG TTT    515
Leu Gln Leu Leu Arg Lys Gly His Glu Val Thr Ile Val Ser Glu Phe
    20              25                  30
```

-continued

| | | | | | | | | | | | | | | | | |
|---|---|---|---|---|---|---|---|---|---|---|---|---|---|---|---|---|
| ACG | CCC | GGT | GAT | CTT | AGT | ATC | GGA | TAT | ACC | TCG | CCT | TGG | GCA | GGT | GCC | 563 |
| Thr | Pro | Gly | Asp | Leu | Ser | Ile | Gly | Tyr | Thr | Ser | Pro | Trp | Ala | Gly | Ala | |
| | 35 | | | | | 40 | | | | 45 | | | | | | |
| AAC | TGG | CTC | ACA | TTT | TAC | GAT | GGA | GGC | AAG | TTA | GCC | GAC | TAC | GAT | GCC | 611 |
| Asn | Trp | Leu | Thr | Phe | Tyr | Asp | Gly | Gly | Lys | Leu | Ala | Asp | Tyr | Asp | Ala | |
| 50 | | | | | 55 | | | | 60 | | | | | | 65 | |
| GTC | TCT | TAT | CCT | ATC | TTG | CGA | GAG | CTG | GCT | CGA | AGC | AGC | CCC | GAG | GCT | 659 |
| Val | Ser | Tyr | Pro | Ile | Leu | Arg | Glu | Leu | Ala | Arg | Ser | Ser | Pro | Glu | Ala | |
| | | | | 70 | | | | | 75 | | | | | 80 | | |
| GGA | ATT | C | | | | | | | | | | | | | | 666 |
| Gly | Ile | | | | | | | | | | | | | | | |

( 2 ) INFORMATION FOR SEQ ID NO:7:

( i ) SEQUENCE CHARACTERISTICS:
        ( A ) LENGTH: 83 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:7:

| | | | | | | | | | | | | | | |
|---|---|---|---|---|---|---|---|---|---|---|---|---|---|---|
| Met | Ala | Lys | Ile | Val | Val | Ile | Gly | Ala | Gly | Val | Ala | Gly | Leu | Thr | Thr |
| 1 | | | | 5 | | | | | 10 | | | | | 15 | |
| Ala | Leu | Gln | Leu | Leu | Arg | Lys | Gly | His | Glu | Val | Thr | Ile | Val | Ser | Glu |
| | | | 20 | | | | | 25 | | | | | 30 | | |
| Phe | Thr | Pro | Gly | Asp | Leu | Ser | Ile | Gly | Tyr | Thr | Ser | Pro | Trp | Ala | Gly |
| | | | 35 | | | | | 40 | | | | | 45 | | |
| Ala | Asn | Trp | Leu | Thr | Phe | Tyr | Asp | Gly | Gly | Lys | Leu | Ala | Asp | Tyr | Asp |
| | 50 | | | | | 55 | | | | | 60 | | | | |
| Ala | Val | Ser | Tyr | Pro | Ile | Leu | Arg | Glu | Leu | Ala | Arg | Ser | Ser | Pro | Glu |
| 65 | | | | | 70 | | | | | 75 | | | | | 80 |
| Ala | Gly | Ile | | | | | | | | | | | | | |

( 2 ) INFORMATION FOR SEQ ID NO:8:

( i ) SEQUENCE CHARACTERISTICS:
        ( A ) LENGTH: 1071 base pairs
        ( B ) TYPE: nucleic acid
        ( C ) STRANDEDNESS: double
        ( D ) TOPOLOGY: unknown ( i i ) MOLECULE TYPE: DNA ( i x ) FEATURE:
        ( A ) NAME/KEY: CDS
        ( B ) LOCATION: join(1..930, 934..936, 940..1068)

( x i ) SEQUENCE DESCRIPTION: SEQ ID NO:8:

| | | | | | | | | | | | | | | | | |
|---|---|---|---|---|---|---|---|---|---|---|---|---|---|---|---|---|
| ATG | GCT | AAA | ATC | GTT | GTT | ATT | GGT | GCC | GGT | GTT | GCC | GGT | TTA | ACT | ACA | 48 |
| Met | Ala | Lys | Ile | Val | Val | Ile | Gly | Ala | Gly | Val | Ala | Gly | Leu | Thr | Thr | |
| 1 | | | | 5 | | | | | 10 | | | | | 15 | | |
| GCT | CTT | CAA | CTT | CTT | CGT | AAA | GGT | CAT | GAG | GTT | ACA | ATT | GTG | TCC | GAG | 96 |
| Ala | Leu | Gln | Leu | Leu | Arg | Lys | Gly | His | Glu | Val | Thr | Ile | Val | Ser | Glu | |
| | | | 20 | | | | | 25 | | | | | 30 | | | |
| TTT | ACG | CCC | GGT | GAT | CTT | AGT | ATC | GGA | TAT | ACC | TCG | CCT | TGG | GCA | GGT | 144 |
| Phe | Thr | Pro | Gly | Asp | Leu | Ser | Ile | Gly | Tyr | Thr | Ser | Pro | Trp | Ala | Gly | |
| | | | 35 | | | | | 40 | | | | | 45 | | | |
| GCC | AAC | TGG | CTC | ACA | TTT | TAC | GAT | GGA | GGC | AAG | TTA | GCC | GAC | TAC | GAT | 192 |
| Ala | Asn | Trp | Leu | Thr | Phe | Tyr | Asp | Gly | Gly | Lys | Leu | Ala | Asp | Tyr | Asp | |
| | 50 | | | | | 55 | | | | | 60 | | | | | |
| GCC | GTC | TCT | TAT | CCT | ATC | TTG | CGA | GAG | CTG | GCT | CGA | AGC | AGC | CCC | GAG | 240 |
| Ala | Val | Ser | Tyr | Pro | Ile | Leu | Arg | Glu | Leu | Ala | Arg | Ser | Ser | Pro | Glu | |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     | 65  |     |     |     | 70  |     |     |     |     | 75  |     |     |     | 80  |     |      |
| GCT | GGA | ATT | CGA | CTC | ATC | AAC | CAA | CGC | TCC | CAT | GTT | CTC | AAG | CGT | GAT | 288  |
| Ala | Gly | Ile | Arg | Leu | Ile | Asn | Gln | Arg | Ser | His | Val | Leu | Lys | Arg | Asp |      |
|     |     |     |     | 85  |     |     |     |     | 90  |     |     |     |     | 95  |     |      |
| CTT | CCT | AAA | CTG | GAA | GGT | GCC | ATG | TCG | GCC | ATC | TGT | CAA | CGC | AAC | CCC | 336  |
| Leu | Pro | Lys | Leu | Glu | Gly | Ala | Met | Ser | Ala | Ile | Cys | Gln | Arg | Asn | Pro |      |
|     |     |     | 100 |     |     |     |     | 105 |     |     |     |     | 110 |     |     |      |
| TGG | TTC | AAA | AAC | ACA | GTC | GAT | TCT | TTC | GAG | ATT | ATC | GAG | GAC | AGG | TCC | 384  |
| Trp | Phe | Lys | Asn | Thr | Val | Asp | Ser | Phe | Glu | Ile | Ile | Glu | Asp | Arg | Ser |      |
|     |     |     | 115 |     |     |     |     | 120 |     |     |     |     | 125 |     |     |      |
| AGG | ATT | GTC | CAC | GAT | GAT | GAG | GCT | TAT | CTA | GTC | GAA | TTT | CGT | TCC | GTT | 432  |
| Arg | Ile | Val | His | Asp | Asp | Glu | Ala | Tyr | Leu | Val | Glu | Phe | Arg | Ser | Val |      |
|     | 130 |     |     |     |     | 135 |     |     |     |     | 140 |     |     |     |     |      |
| TGT | ATC | CAC | ACC | GGA | GTC | TAC | TTG | AAC | TGG | CTG | ATG | TCC | CAA | TGC | TTA | 480  |
| Cys | Ile | His | Thr | Gly | Val | Tyr | Leu | Asn | Trp | Leu | Met | Ser | Gln | Cys | Leu |      |
| 145 |     |     |     |     | 150 |     |     |     |     | 155 |     |     |     |     | 160 |      |
| TCG | CTC | GGC | GCC | ACG | GTG | GTT | AAA | CGT | CGA | GTG | AAC | CAT | ATC | AAG | GAT | 528  |
| Ser | Leu | Gly | Ala | Thr | Val | Val | Lys | Arg | Arg | Val | Asn | His | Ile | Lys | Asp |      |
|     |     |     |     | 165 |     |     |     |     | 170 |     |     |     |     | 175 |     |      |
| GCC | AAT | TTA | CTA | CAC | TCC | TCA | GGA | TCA | CGC | CCC | GAC | GTG | ATT | GTC | AAC | 576  |
| Ala | Asn | Leu | Leu | His | Ser | Ser | Gly | Ser | Arg | Pro | Asp | Val | Ile | Val | Asn |      |
|     |     |     | 180 |     |     |     |     | 185 |     |     |     |     | 190 |     |     |      |
| TGT | AGT | GGT | CTC | TTT | GCC | CGG | TTC | TTG | GGA | GGC | GTC | GAG | GAC | AAG | AAG | 624  |
| Cys | Ser | Gly | Leu | Phe | Ala | Arg | Phe | Leu | Gly | Gly | Val | Glu | Asp | Lys | Lys |      |
|     |     | 195 |     |     |     |     | 200 |     |     |     |     | 205 |     |     |     |      |
| ATG | TAC | CCT | ATT | CGA | GGA | CAA | GTC | GTC | CTT | GTT | CGA | AAC | TCT | CTT | CCT | 672  |
| Met | Tyr | Pro | Ile | Arg | Gly | Gln | Val | Val | Leu | Val | Arg | Asn | Ser | Leu | Pro |      |
|     | 210 |     |     |     |     | 215 |     |     |     |     | 220 |     |     |     |     |      |
| TTT | ATG | GCC | TCC | TTT | TCC | AGC | ACT | CCT | GAA | AAA | GAA | AAT | GAA | GAC | GAA | 720  |
| Phe | Met | Ala | Ser | Phe | Ser | Ser | Thr | Pro | Glu | Lys | Glu | Asn | Glu | Asp | Glu |      |
| 225 |     |     |     |     | 230 |     |     |     |     | 235 |     |     |     |     | 240 |      |
| GCT | CTA | TAT | ATC | ATG | ACC | CGA | TTC | GAT | GGT | ACT | TCT | ATC | ATT | GGC | GGT | 768  |
| Ala | Leu | Tyr | Ile | Met | Thr | Arg | Phe | Asp | Gly | Thr | Ser | Ile | Ile | Gly | Gly |      |
|     |     |     |     | 245 |     |     |     |     | 250 |     |     |     |     | 255 |     |      |
| TGT | TTC | CAA | CCC | AAC | AAC | TGG | TCA | TCC | GAA | CCC | GAT | CCT | TCT | CTC | ACC | 816  |
| Cys | Phe | Gln | Pro | Asn | Asn | Trp | Ser | Ser | Glu | Pro | Asp | Pro | Ser | Leu | Thr |      |
|     |     |     | 260 |     |     |     |     | 265 |     |     |     |     | 270 |     |     |      |
| CAT | CGA | ATC | CTG | TCT | AGA | GCC | CTC | GAC | CGA | TTC | CCG | GAA | CTG | ACC | AAA | 864  |
| His | Arg | Ile | Leu | Ser | Arg | Ala | Leu | Asp | Arg | Phe | Pro | Glu | Leu | Thr | Lys |      |
|     |     | 275 |     |     |     |     | 280 |     |     |     |     | 285 |     |     |     |      |
| GAT | GGC | CCT | CTT | GAC | ATT | GTG | CGC | GAA | TGC | GTT | GGC | CAC | CGT | CCT | GGT | 912  |
| Asp | Gly | Pro | Leu | Asp | Ile | Val | Arg | Glu | Cys | Val | Gly | His | Arg | Pro | Gly |      |
|     | 290 |     |     |     |     | 295 |     |     |     |     | 300 |     |     |     |     |      |
| AGA | GAG | GGC | GGT | CCC | CGA | GTA | GAA | TTA | GAG | AAG | ATC | CCC | GGC | GTT | GGC | 960  |
| Arg | Glu | Gly | Gly | Pro | Arg |     | Glu |     | Glu | Lys | Ile | Pro | Gly | Val | Gly |      |
| 305 |     |     |     |     | 310 |     |     |     |     | 315 |     |     |     |     |     |      |
| TTT | GTT | GTC | CAT | AAC | TAT | GGT | GCC | GCC | GGT | GCT | GGT | TAC | CAA | TCC | TCT | 1008 |
| Phe | Val | Val | His | Asn | Tyr | Gly | Ala | Ala | Gly | Ala | Gly | Tyr | Gln | Ser | Ser |      |
|     | 320 |     |     |     |     | 325 |     |     |     |     | 330 |     |     |     |     |      |
| TAC | GGC | ATG | GCT | GAT | GAA | GCT | GTT | TCT | TAC | GTC | GAA | AGA | GCT | CTT | ACT | 1056 |
| Tyr | Gly | Met | Ala | Asp | Glu | Ala | Val | Ser | Tyr | Val | Glu | Arg | Ala | Leu | Thr |      |
| 335 |     |     |     | 340 |     |     |     |     | 345 |     |     |     |     | 350 |     |      |
| CGT | CCA | AAC | CTT | TAG |     |     |     |     |     |     |     |     |     |     |     | 1071 |
| Arg | Pro | Asn | Leu |     |     |     |     |     |     |     |     |     |     |     |     |      |

( 2 ) INFORMATION FOR SEQ ID NO:9:

( i ) SEQUENCE CHARACTERISTICS:
        ( A ) LENGTH: 354 amino acids
        ( B ) TYPE: amino acid (D) TOPOLOGY: unknown (ii) MOLECULE TYPE: protein (xi) SEQUENCE DESCRIPTION: SEQ ID NO:9:

| Met | Ala | Lys | Ile | Val | Val | Ile | Gly | Ala | Gly | Val | Ala | Gly | Leu | Thr | Thr |
|---|---|---|---|---|---|---|---|---|---|---|---|---|---|---|---|
| 1 | | | | 5 | | | | | 10 | | | | | 15 | |
| Ala | Leu | Gln | Leu | Leu | Arg | Lys | Gly | His | Glu | Val | Thr | Ile | Val | Ser | Glu |
| | | | 20 | | | | | 25 | | | | | 30 | | |
| Phe | Thr | Pro | Gly | Asp | Leu | Ser | Ile | Gly | Tyr | Thr | Ser | Pro | Trp | Ala | Gly |
| | | 35 | | | | | 40 | | | | | 45 | | | |
| Ala | Asn | Trp | Leu | Thr | Phe | Tyr | Asp | Gly | Gly | Lys | Leu | Ala | Asp | Tyr | Asp |
| | 50 | | | | | 55 | | | | | 60 | | | | |
| Ala | Val | Ser | Tyr | Pro | Ile | Leu | Arg | Glu | Leu | Ala | Arg | Ser | Ser | Pro | Glu |
| 65 | | | | | 70 | | | | | 75 | | | | | 80 |
| Ala | Gly | Ile | Arg | Leu | Ile | Asn | Gln | Arg | Ser | His | Val | Leu | Lys | Arg | Asp |
| | | | | 85 | | | | | 90 | | | | | 95 | |
| Leu | Pro | Lys | Leu | Glu | Gly | Ala | Met | Ser | Ala | Ile | Cys | Gln | Arg | Asn | Pro |
| | | | 100 | | | | | 105 | | | | | 110 | | |
| Trp | Phe | Lys | Asn | Thr | Val | Asp | Ser | Phe | Glu | Ile | Ile | Glu | Asp | Arg | Ser |
| | | 115 | | | | | 120 | | | | | 125 | | | |
| Arg | Ile | Val | His | Asp | Asp | Glu | Ala | Tyr | Leu | Val | Glu | Phe | Arg | Ser | Val |
| | 130 | | | | | 135 | | | | | 140 | | | | |
| Cys | Ile | His | Thr | Gly | Val | Tyr | Leu | Asn | Trp | Leu | Met | Ser | Gln | Cys | Leu |
| 145 | | | | | 150 | | | | | 155 | | | | | 160 |
| Ser | Leu | Gly | Ala | Thr | Val | Val | Lys | Arg | Arg | Val | Asn | His | Ile | Lys | Asp |
| | | | | 165 | | | | | 170 | | | | | 175 | |
| Ala | Asn | Leu | Leu | His | Ser | Ser | Gly | Ser | Arg | Pro | Asp | Val | Ile | Val | Asn |
| | | | 180 | | | | | 185 | | | | | 190 | | |
| Cys | Ser | Gly | Leu | Phe | Ala | Arg | Phe | Leu | Gly | Gly | Val | Glu | Asp | Lys | Lys |
| | | 195 | | | | | 200 | | | | | 205 | | | |
| Met | Tyr | Pro | Ile | Arg | Gly | Gln | Val | Val | Leu | Val | Arg | Asn | Ser | Leu | Pro |
| | 210 | | | | | 215 | | | | | 220 | | | | |
| Phe | Met | Ala | Ser | Phe | Ser | Ser | Thr | Pro | Glu | Lys | Glu | Asn | Glu | Asp | Glu |
| 225 | | | | | 230 | | | | | 235 | | | | | 240 |
| Ala | Leu | Tyr | Ile | Met | Thr | Arg | Phe | Asp | Gly | Thr | Ser | Ile | Ile | Gly | Gly |
| | | | | 245 | | | | | 250 | | | | | 255 | |
| Cys | Phe | Gln | Pro | Asn | Asn | Trp | Ser | Ser | Glu | Pro | Asp | Pro | Ser | Leu | Thr |
| | | | 260 | | | | | 265 | | | | | 270 | | |
| His | Arg | Ile | Leu | Ser | Arg | Ala | Leu | Asp | Arg | Phe | Pro | Glu | Leu | Thr | Lys |
| | | 275 | | | | | 280 | | | | | 285 | | | |
| Asp | Gly | Pro | Leu | Asp | Ile | Val | Arg | Glu | Cys | Val | Gly | His | Arg | Pro | Gly |
| | 290 | | | | | 295 | | | | | 300 | | | | |
| Arg | Glu | Gly | Gly | Pro | Arg | Glu | Glu | Lys | Ile | Pro | Gly | Val | Gly | Phe | Val |
| 305 | | | | | 310 | | | | | 315 | | | | | 320 |
| Val | His | Asn | Tyr | Gly | Ala | Ala | Gly | Ala | Gly | Tyr | Gln | Ser | Ser | Tyr | Gly |
| | | | | 325 | | | | | 330 | | | | | 335 | |
| Met | Ala | Asp | Glu | Ala | Val | Ser | Tyr | Val | Glu | Arg | Ala | Leu | Thr | Arg | Pro |
| | | | 340 | | | | | 345 | | | | | 350 | | |
| Asn | Leu | | | | | | | | | | | | | | |

(2) INFORMATION FOR SEQ ID NO:10:

(i) SEQUENCE CHARACTERISTICS:
(A) LENGTH: 27 base pairs ( B ) TYPE: nucleic acid
                ( C ) STRANDEDNESS: double
                ( D ) TOPOLOGY: unknown ( i i ) MOLECULE TYPE: DNA ( i x ) FEATURE:
                ( A ) NAME/KEY: misc_feature
                ( B ) LOCATION: 14
                ( D ) OTHER INFORMATION: /note="N is an internal nucleic
                        acid sequence of unspecified length, which is
                        shown as a "--"in the figure."

( x i ) SEQUENCE DESCRIPTION: SEQ ID NO:10:

CGGATCCGAA TTCNAAGCTC GGATCCG                                        27

( 2 ) INFORMATION FOR SEQ ID NO:11:

( i ) SEQUENCE CHARACTERISTICS:
                ( A ) LENGTH: 27 base pairs
                ( B ) TYPE: nucleic acid
                ( C ) STRANDEDNESS: double
                ( D ) TOPOLOGY: unknown ( i i ) MOLECULE TYPE: DNA ( i v ) ANTI-SENSE: YES ( i x ) FEATURE:
                ( A ) NAME/KEY: misc_feature
                ( B ) LOCATION: 14
                ( D ) OTHER INFORMATION: /note="N is an internal nucleic
                        acid sequence of unspecified length."

( x i ) SEQUENCE DESCRIPTION: SEQ ID NO:11:

CGGATCCGAG CTTNGAATTC GGATCCG                                        27

( 2 ) INFORMATION FOR SEQ ID NO:12:

( i ) SEQUENCE CHARACTERISTICS:
                ( A ) LENGTH: 30 base pairs
                ( B ) TYPE: nucleic acid
                ( C ) STRANDEDNESS: single
                ( D ) TOPOLOGY: unknown ( i i ) MOLECULE TYPE: DNA ( i x ) FEATURE:
                ( A ) NAME/KEY: intron
                ( B ) LOCATION: 14..18

( i x ) FEATURE:
                ( A ) NAME/KEY: misc_feature
                ( B ) LOCATION: 16
                ( D ) OTHER INFORMATION: /note="N is an intron of
                        unspecified nucleic acid sequence length."

( x i ) SEQUENCE DESCRIPTION: SEQ ID NO:12:

TCGTTGTTAT TGGGTNAGTG CCGGTGTTGC                                     30

( 2 ) INFORMATION FOR SEQ ID NO:13:

( i ) SEQUENCE CHARACTERISTICS:
                ( A ) LENGTH: 25 base pairs
                ( B ) TYPE: nucleic acid
                ( C ) STRANDEDNESS: single
                ( D ) TOPOLOGY: unknown ( i i ) MOLECULE TYPE: DNA ( i v ) ANTI-SENSE: YES ( x i ) SEQUENCE DESCRIPTION: SEQ ID NO:13:

GCAACACCGG CACCAATAAC AACGA                                                                                    25

( 2 ) INFORMATION FOR SEQ ID NO:14:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: unknown ( i i ) MOLECULE TYPE: DNA ( x i ) SEQUENCE DESCRIPTION: SEQ ID NO:14:

TCGTTGTTAA TGTTGCCGGT GTTGC                                                                                    25

( 2 ) INFORMATION FOR SEQ ID NO:15:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: unknown ( i i ) MOLECULE TYPE: DNA ( i x ) FEATURE:
        ( A ) NAME/KEY: intron
        ( B ) LOCATION: 14..17
        ( D ) OTHER INFORMATION: /note="N is a non-coding intron of
            unspecified length."

( x i ) SEQUENCE DESCRIPTION: SEQ ID NO:15:

CTCTAGAGGA TCCNAAAATG GCTAAAATC                                                                                29

( 2 ) INFORMATION FOR SEQ ID NO:16:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: unknown ( i i ) MOLECULE TYPE: DNA ( i v ) ANTI-SENSE: YES ( x i ) SEQUENCE DESCRIPTION: SEQ ID NO:16:

GATTTTAGCC ATGGATCCTC TAGAG                                                                                    25

( 2 ) INFORMATION FOR SEQ ID NO:17:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: unknown ( i i ) MOLECULE TYPE: DNA ( x i ) SEQUENCE DESCRIPTION: SEQ ID NO:17:

CTCTAGAGGA TCCATGGCTA AAATC                                                                                    25